United States Patent [19]

Keller

[11] 4,364,389
[45] Dec. 21, 1982

[54] INSTRUMENT FOR HOLDING AND INSERTING THE TIBIA PLATE FOR AN ENDO-KNEE PROSTHESIS HAVING SLIDING SURFACES

[75] Inventor: Arnold Keller, Kayhude, Fed. Rep. of Germany

[73] Assignee: Waldemar Link GmbH & Co., Hamburg, Fed. Rep. of Germany

[21] Appl. No.: 244,627

[22] Filed: Mar. 17, 1981

[30] Foreign Application Priority Data

Mar. 19, 1980 [DE] Fed. Rep. of Germany ....... 3010421

[51] Int. Cl.³ .............................................. A61B 17/00
[52] U.S. Cl. .................................. 128/303 R; 3/1.911
[58] Field of Search .............. 128/92 R, 92 E, 92 EA, 128/303 R; 3/1.911

[56] References Cited

U.S. PATENT DOCUMENTS

3,750,652 8/1973 Sherwin .......................... 128/303 R
4,147,167 4/1979 Hickmann et al. .............. 128/303 R

*Primary Examiner*—John D. Yasko
*Attorney, Agent, or Firm*—Prutzman, Kalb, Chilton & Alix

[57] ABSTRACT

A prosthesis instrument for implanting a pair of separate tibia plates of an endo-knee prosthesis and having a pair of supports with tibia plate locating rods and clamps for rigidly supporting the tibia plates and laterally adjustable for establishing a predetermined implanted relationship thereof.

13 Claims, 3 Drawing Figures

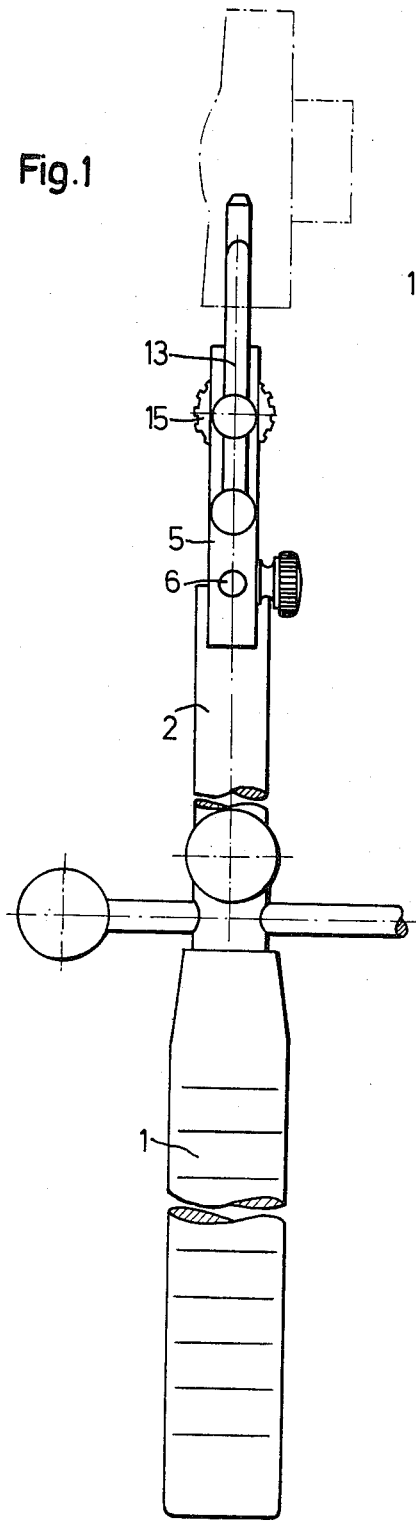
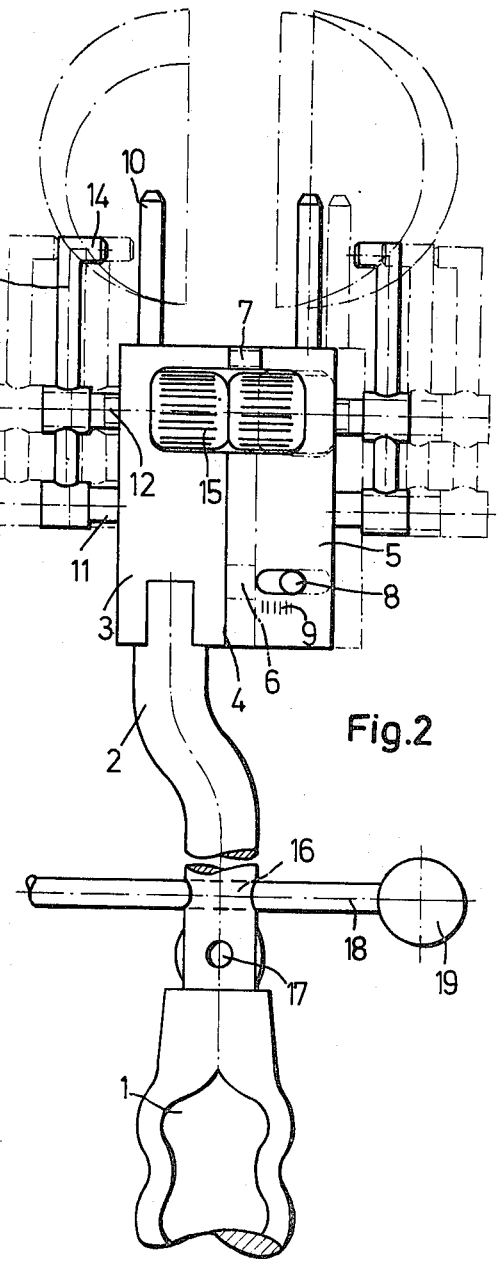
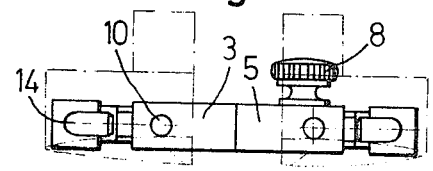
Fig.1
Fig.2
Fig.3

INSTRUMENT FOR HOLDING AND INSERTING THE TIBIA PLATE FOR AN ENDO-KNEE PROSTHESIS HAVING SLIDING SURFACES

Description

TECHNICAL FIELD

The invention relates to a prosthesis instrument for holding and inserting a tibia plate for an endo-knee prosthesis having sliding surfaces.

A prosthesis of the aforementioned kind comprises "tibia plates" on the tibia side and metal runners on the femur side. The tibia plates of the prosthesis may be plastic plates which replace the horizontally worn tibia plates. In total endo-prosthesis with sliding surfaces, use is generally made of U-shaped plastic tibia plates which form a single component replacement for the two tibia plates. Such has the advantage of ensuring that both sides of the two tibia plates are aligned in exactly matching positions. However, two separate individual tibia plates have also been employed in an endo-knee prosthesis because they become loose less frequently than the single component tibia plate.

DISCLOSURE OF INVENTION

The object of the present invention is to provide an endo-knee prosthesis instrument of the type described which provides for employing the advantages of both of the aforementioned known kinds of tibia plates prosthesis.

The solution according to the present invention is the provision of a prosthesis instrument or tool for mounting individual tibia plates in an exactly matching position. The instrument or tool is characterized in comprising means for rigidly holding the two tibia plates relative to one another in a desired predetermined association.

In accordance with the present invention, the prosthesis instrument provides for mounting the two tibia plates in an exact fixed position relative to one another without the use of a mechanical connection between the plates which might substantially loosen the plates after they are implanted.

Advantageously, according to the present invention, the instrument employs means for accurately preadjusting the relative positions of the tibia plates and yet for rigidly holding the tibia plates in their adjusted predetermined association while they are implanted and fully secured.

Advantageously, the means for mounting each tibia plate comprises an elongated locating rod rigidly connected to the instrument and received tightly in a corresponding longitudinal bore in the tibia plate. Also, the mounting means comprises a clamp adjustable transversely of the locating rod to clamp the tibia plate to the rod and thereby lock the tibia plate from shifting longitudinally or pivoting on the rod. Advantageously, the clamp comprises a rod section extending normal to the locating rod for receipt if required within a corresponding bore in the tibia plate.

According to the present invention, the instrument comprises two separate tibia plate supports which can be adjusted relatively to each other for adjusting the relative positions of the two tibia plates of the prosthesis. For that purpose, the instrument comprises a first fixed tibia plate support secured onto the forward end of a handle of the instrument and a second adjustable tibia plate support laterally adjustable relative to the first fixed support via a transverse guide interconnecting the two tibia plate supports. Alternatively, both tibia plate supports can be mounted to be laterally adjustable, but, it is more advantageous and simpler to provide only one adjustable tibia plate support. Any one of a number of known types of adjustable guides can be used to connect the two tibia plate supports for relative adjustment, including means which provide adequate but not theoretically exact linear relative adjustment. For example, the two tibia plate supports can be mounted on the ends of two arms which are pivotably interconnected so that the two supports can be relatively adjusted along an arc.

Advantageously, a linear adjustment is also provided between each elongated locating rod and its associated clamp. Preferably, each elongated locating rod is secured directly to one of the tibia plate supports, whereas the clamp is mounted for example by transverse guide rods slidable in the respective tibia plate support for linear adjustment transversely and preferably normal to the axis of the locating rod. Alternatively, the clamp can be mounted for pivotal movement transversely of the locating rod.

Advantageously, a threaded spindle and knurled nut are provided for adjusting the clamp on its tibia plate support since such provides an easy and simple clamp adjustment. Also, similar adjusting means can be used for adjusting the lateral distance between the two tibia plate supports. Usually, however, manual adjustment of the lateral distance between the two tibia plate supports is sufficient because the forces to be overcome are small and because the two tibia plate supports can be exactly adjusted in advance during preparation for the prosthesis operation. Also, according to the invention, adjustment is simplified by the provision of a scale on the instrument for determining the relative positions of the two tibia plate supports.

The tibia plates must be installed in the correct position relative to certain reference directions, i.e. the top edge of the tibia and the axis of the lower leg bone. To this end, according to another feature of the present invention, the instrument is provided with means for forming linear reference edges or axes which remain at fixed angles to the tibia plate supports and to their linear direction of lateral adjustment. Preferably, the linear reference edges are provided by rods which are detachably insertable into mounting guides of the instrument which can be provided very simply by transverse bores in the handle.

Other objects and advantages of the present invention will be in part obvious and in part pointed out more in detail hereinafter.

A better understanding of the invention will be obtained from the following detailed description and the accompanying drawing of an illustrative application of the invention.

BRIEF DESCRIPTION OF DRAWING

FIG. 1 is a side view, partly broken away and partly in section, of an instrument incorporating an embodiment of the present invention for holding and inserting the tibia plates for an endo-knee prosthesis having sliding surfaces, and additionally showing in broken lines a tibia plate member supported by the instrument;

FIG. 2 is a top plan view, partly broken away and partly in section, of the instrument, additionally showing in broken lines tibia plate members supported by the instrument; and FIG. 3 is a front end view of the instrument, additionally showing in broken lines tibia plate members supported by the instrument.

BEST MODE FOR CARRYING OUT THE INVENTION

Referring now to the drawing in detail, an instrument incorporating an embodiment of the present invention for holding and inserting the tibia plates for an endo-knee prosthesis having sliding surfaces is shown having an elongated handle or grip 1 with a rigid longitudinally extending rod 2. The rod 2 is suitably fixed to a generally flat rectangular support plate or block 3. The plate 3 provides a support or bearing member and has a flat side face 4 (on the right side of the support 3 as it is viewed in FIG. 2) which, because of a lateral offset between the ends of the rod 2 provided by an intermediate S-shaped section of the rod, lies on the longitudinal center line of the handle 1.

A second slide support plate or block 5 similar to the fixed support plate 3 has a pair of transverse bores for receiving a pair of transverse guide rods or pins 6,7 fixed within bores in the fixed support plate 3 and extending normal to its side face 4. The slide plate 5 is thereby adapted to be transversely adjusted on the guide rods 6,7 (normal to the side face 4 and center line of the instrument handle 1) between an inner withdrawn position shown in full lines in FIG. 2 where the slide plate 5 engages the side face 4 of the fixed support plate 3 and an outer extended position shown outlined in broken lines in FIG. 2 where the slide plate 5 is spaced laterally outwardly of the support plate 3. The guide rods 6,7 are visible when the slide plate 5 is in its outer extended position spaced from the fixed support plate 3.

A lower upright locking knob 8 is threaded into the guide rod 6 and can be tightened into locking engagement with the slide plate 5 to lock it in its adjusted position. The locking knob 8 is loosened to adjust the slide plate 5 relative to the fixed support plate 3 and is then retightened to lock the slide plate 5 in position. A slot is provided in the slide plate 5 for receiving the threaded stud of the locking knob 8 and provides for establishing the outer limits of adjustment of the slide plate 5 relative to the fixed support plate 3. Also, a scale 9 is provided on the top planar edge of the slide plate 5 adjacent the slot to facilitate establishing the desired relative positions of the slide and support plates (and as hereinafter more fully understood, for thereby establishing the desired predetermined relative positions of two tibia plate members supported by the instrument).

Tibia plate mounting means is provided on each of the support plates 3,5, but since the two tibia plate mounting means are substantially identical only the tibia plate mounting means provided on the fixed block 3 is identified with reference numerals. Each such tibia plate mounting means comprises an elongated locating rod or pin 10 extending parallel to the primary axis or center line of the handle 1 and to the flat side face 4 of the fixed plate 3. The two locating rods 10 are fixed within bores in the support plates 3,5 respectively and are parallel to each other. Their lateral spacing is dependent on the adjusted relative lateral positions of the plates 3,5. Also, each support plate 3,5 has a pair of transverse linear bores for slidably receiving a pair of transverse guide rods 11,12 of a tibia plate clamp. The outer ends of the guide rods 11,12 are fixed to an elongated rod section 13 of the clamp which has an outer right angle rod section 14 extending inwardly toward and perpendicular to the adjacent locating rod 10. The two outer rod sections 14 also extend parallel to their respective guide rods 11,12 and are and remain coaxial as each clamp is linearly adjusted relative to its support plate 3,5 and as the two support plates 3,5 are relatively laterally adjusted. Each guide rod 12 is threaded to form an adjustment spindle. An enlarged knurled adjustment nut 15 is mounted on the threaded spindle and received within a suitable slot in the respective support plate 3,5. Each knurled adjustment nut 15 is therefore adapted to be manually rotated to shift the respective tibia plate clamp laterally of the locating rod 10 to facilitate mounting and rigidly supporting a tibia plate at the forward end of the instrument. Also, each tibia plate member, whether it be relatively large or relatively small as shown in broken lines at the top left of FIG. 2, is provided with suitable bores for receiving the ends of the locating rod 10 and clamping rod section 14 so that each selected tibia plate member may be accurately located and rigidly held in position.

If desired, threaded adjustment spindle (not shown) can be provided between the two support plates 3,5 to facilitate establishing their relative lateral positions. Such a threaded adjustment spindle, which may be employed in addition to the guide rods 6,7, may for example have right hand and left hand threaded sections received with threaded lateral bores in the support plates 3,5. A central knurled wheel of the threaded adjustment spindle could then be used for rotating the spindle and thereby adjust the relative lateral positions of the support plates 3,5. The locking knob 8 would still be employed to rigidly lock the two support plates 3,5 at their adjusted relative positions.

The handle rod 2 has a pair of transverse bores 16,17 which extend perpendicular to each other and parallel to the two principal transverse axes of the instrument. In particular, the transverse bore 16 extends parallel to the common plane of the locating rods 10 and therefore parallel to the common plane of the tibia plate members supported and clamped in position on the locating rods 10. The transverse bore 16 therefore also extends parallel to the linear axis of adjustment of the clamps and the linear axis of relative adjustment of the two support plates 3,5. The second transverse bore 17 extends perpendicular to the transverse bore 16 and perpendicular to the common planes of the locating rods 10.

A reference rod 18 with a spherical knob 19 on its outer end is mounted in each of the transverse guide bores 16,17 to facilitate accurately positioning the supported tibia plate members with the instrument. Each reference rod 18 is dimensioned to be rigidly mounted within its guide bore and yet to be removed when desired, for example, when the reference rod is not needed and for those applications where it may be a hindrance. The knobs 19 at the outer ends of the reference rods 18 are provided for ease in manipulating the instrument and to facilitate comparing and matching the two reference axes of the instrument provided by the two rods 18 with selected reference axes of the patient, for example, the axes of the patient's lower leg bone and the milling on the tibia heads.

As will be apparent to persons skilled in the art, various modifications, adaptations and variations of the foregoing specific disclosure can be made without departing from the teachings of the present invention.

I claim:

1. A prosthesis instrument for holding and inserting a pair of tibia plate members for an endo-knee prosthesis having sliding surfaces, comprising an instrument support handle, a pair of tibia plate support means on the support handle for rigidly supporting a pair of tibia plate members respectively in predetermined lateral relationship for holding and inserting them for said prosthesis, the pair of tibia plate support means being relatively laterally adjustable for adjusting the said predetermined lateral relationship of the said tibia plate members, and reference edges disposed at fixed angles to the pair of tibia plate support means in the direction in which they are relatively laterally adjusted.

2. A prosthesis instrument according to claim 1 wherein the instrument comprises elongated laterally extending reference rods mounted on the support handle to form the reference edges.

3. A prosthesis instrument according to claim 2 wherein the instrument support handle has transverse bores detachably supporting the elongated reference rods.

4. A prosthesis instrument for holding and inserting a pair of tibia plate members for an endo-knee prosthesis having sliding surfaces, comprising an instrument support handle, a pair of tibia plate support means mounted on the support handle for rigidly supporting a pair of tibia plate members respectively in predetermined lateral relationship for holding and inserting them for said prosthesis, the pair of tibia plate support means being relatively laterally adjustable for adjusting the said predetermined lateral relationship of the said tibia plate members, and a scale for determining the relative lateral position of the pair of tibia plate support means.

5. A prosthesis instrument for holding and inserting a pair of tibia plate members for an endo-knee prosthesis having sliding surfaces, comprising an instrument support handle and a pair of tibia plate support means on the support handle for rigidly supporting a pair of tibia plate members respectively in predetermined lateral relationship for holding and inserting them for said prosthesis, the pair of tibia plate support means being relatively laterally adjustable for adjusting the said predetermined lateral relationship of the said tibia plate members, and each of said tibia plate support means comprising an elongated locating rod for supporting a tibia plate member thereon and a clamp adjustable laterally of the axis of the locating rod for clamping a tibia plate member therebetween.

6. A prosthesis instrument according to claim 5 wherein each clamp comprises a rod section extending transversely of the elongated locating rod of the respective tibia plate support means for clamping a tibia plate member therebetween.

7. A prosthesis instrument according to claim 5 wherein the pair of tibia plate support means comprises two separate support members respectively, each supporting a respective elongated locating rod and adjustable clamp, and wherein the instrument further comprises guide means interconnecting the separate support members for relative lateral adjustment thereof for laterally adjusting the said predetermined relationship of the tibia plate members.

8. A prosthesis instrument according to claim 7 wherein each clamp comprises lateral guide means laterally adjustable on the respective support member for laterally adjusting the clamp relative thereto.

9. A prosthesis instrument according to claim 8 wherein each clamp comprises a threaded spindle and a threaded adjustment nut mounted on the spindle for laterally adjusting the clamp relative to its support member.

10. In a prosthesis instrument for holding and inserting a pair of tibia plate members for an endo-knee prosthesis having sliding surfaces, comprising an instrument body with a support handle and a pair of tibia plate supports mounted on the support handle, holding means mounted on each tibia plate support for rigidly supporting a tibia plate member, for rigidly supporting with both holding means a pair of tibia plate members in predetermined lateral relationship for holding and inserting them for said prosthesis, the instrument body having first adjustment means for laterally adjusting the pair of tibia plate supports for adjusting the said predetermined lateral relationship of the said tibia plate members, the improvement wherein each tibia plate member holding means comprises a first longitudinally extending support rod receivable in a longitudinally extending bore in a tibia plate member, a second laterally extending support rod lying in substantially the same plane as the first rod, and second adjustment means for laterally adjusting the second support rod into a laterally extending bore in the tibia plate member for rigidly supporting the tibia plate member with the first and second support rods.

11. A prosthesis instrument according to claim 10 wherein the first adjustment means comprises a pair of laterally extending parallel guide rods, each secured to one of said supports and received within a lateral bore in the other support.

12. A prosthesis instrument according to claim 10 or 11 wherein said second adjustment means comprises a pair of laterally extending parallel guide rods supporting said second laterally extending rod and received within a pair of lateral bores in the support for laterally adjusting the second support rod, and adjustment knob means mounted one of the guide rods and rotatable to laterally adjust the guide rods and therefore said second support rod.

13. A prosthesis instrument according to claim 10 or 11 further comprising a scale for determining the relative lateral positions of the pair of tibia plate supports.

* * * * *